United States Patent
Chen (10) Patent No.: US 10,780,293 B2
(45) Date of Patent: Sep. 22, 2020

(54) WEARABLE LIGHT EMITTING APPARATUS FOR EYEBROW GROWTH

(71) Applicant: Chung-Yang Chen, Xindian (TW)

(72) Inventor: Chung-Yang Chen, Xindian (TW)

(*) Notice: Subject to any disclaimer, the term of this patent is extended or adjusted under 35 U.S.C. 154(b) by 202 days.

(21) Appl. No.: 15/868,202

(22) Filed: Jan. 11, 2018

(65) Prior Publication Data

US 2019/0209860 A1  Jul. 11, 2019

(51) Int. Cl.
| | |
|---|---|
| *A61N 5/06* | (2006.01) |
| *F21V 21/084* | (2006.01) |
| *F21V 15/01* | (2006.01) |
| *F21S 9/02* | (2006.01) |
| *F21Y 115/10* | (2016.01) |
| *F21V 11/00* | (2015.01) |

(52) U.S. Cl.
CPC ........... *A61N 5/0617* (2013.01); *F21V 15/01* (2013.01); *F21V 21/084* (2013.01); *A61N 2005/0647* (2013.01); *A61N 2005/0651* (2013.01); *F21S 9/02* (2013.01); *F21V 11/00* (2013.01); *F21Y 2115/10* (2016.08)

(58) Field of Classification Search
CPC .......... A61N 5/0617; A61N 2005/0647; A61N 2005/0651; F21V 21/084; F21V 15/01; F21V 11/00; F21Y 2115/10; F21S 9/02
See application file for complete search history.

(56) References Cited

U.S. PATENT DOCUMENTS

| | | | |
|---|---|---|---|
| 10,272,259 B1* | 4/2019 | Blanche | A61N 5/0617 |
| 2008/0262575 A1* | 10/2008 | Aunio | A61M 21/00 |
| | | | 607/88 |
| 2013/0041432 A1* | 2/2013 | Tucker | A61N 5/0617 |
| | | | 607/89 |
| 2015/0224339 A1* | 8/2015 | Unger | A61N 5/0617 |
| | | | 607/79 |
| 2016/0056653 A1* | 2/2016 | Tapper | A61N 5/0616 |
| | | | 607/91 |
| 2017/0340897 A1* | 11/2017 | Unger | A61N 5/0617 |

* cited by examiner

*Primary Examiner* — Gary Jackson
*Assistant Examiner* — Sebastian X Lukjan
(74) *Attorney, Agent, or Firm* — Muncy, Geissler, Olds & Lowe, P.C.

(57) ABSTRACT

A wearable light emitting apparatus for eyebrow growth is provided. The wearable light emitting apparatus for eyebrow growth comprises a main body and at least one light emitting assembly. The main body is to be wore on an user's head. The at least one light emitting assembly is located on the main body for projecting at least an eyebrow-shaped light beam to an eyebrow growing area of the head when the main body is wore on the user's head.

5 Claims, 9 Drawing Sheets

WEARABLE LIGHT EMITTING APPARATUS FOR EYEBROW GROWTH

BACKGROUND OF INVENTION

1. Field of the Invention

The present invention is related to a wearable light emitting apparatus for eyebrow growth, and more particularly is related to a wearable light emitting apparatus for eyebrow growth capable of emitting an eyebrow-shaped light beam to an eyebrow growing area.

2. Description of the Prior Art

In general, the basic function of the eyebrows is to prevent sweat or rain from falling into the eye. The downward curve at the outward edge of the eyebrow makes sure that the moisture has a tendency to flow along the eyebrow to the position outside the eyes so as to prevent the moisture from falling into the eyes directly. In addition, the existence of the eyebrows is also helpful for preventing some small objects, such as hairs, dandruff, or small insects, from falling into the eyes.

As mentioned, in addition to the aforementioned basic functions, the eyebrow is also capable to assist facial expression, e.g. to strengthen emotional appear by the motions such as to knit one's eyebrows or to raise one's eyebrows. In addition, because facial appearance is the most direct impression for human communication, many people ask for a perfect face, and the shape of eyebrows is certainly an indispensable part.

In order to have the shape of eyebrows matching the aesthetic preference of the public better, most users shape the eyebrows by using the method such as trimming, tattooing, drawing, and etc. However, a long time of trimming or plucking treatment to the eyebrow hairs may make the eyebrows sparse. In addition, the eyebrows may also become sparse or shed under the influence of pressure, emotion or genes. Then, the users can only choose the methods such as tattooing or drawing to improve the appearance of eyebrows, or choose the methods such as the eyebrow growth liquid or eyebrow implantation to increase the amount of eyebrow hairs.

Although there have many different methods available for shaping the eyebrows, however, most of the methods can only shape the existing eyebrows. Such methods would leave some unnatural feeling or even damage the growing area of the eyebrows.

SUMMARY OF THE INVENTION

In view of the conventional technologies mentioned above, most of the eyebrow shaping methods are executed manually to modify the shape of eyebrows, which would cause an unnatural feeling or even damage the growing area of eyebrows during the shaping process due to a poor shaping skill and further cause the problem of slim or sparse eyebrows. Accordingly, it is a main object of the present invention to provide a wearable light emitting apparatus for eyebrow growth.

In accordance with the aforementioned object, a wearable light emitting apparatus for eyebrow growth is provided in the present invention. The wearable light emitting apparatus for eyebrow growth comprises a main body and at least one light emitting assembly. The main body is to be wore on an user's head. The at least one light emitting assembly is located on the main body, for projecting at least an eyebrow-shaped light beam to an eyebrow growing area of the head when the main body is wore on the user's head.

In accordance with an embodiment of the present invention, the at least one light emitting assembly comprises at least one light emitting element, a light shield fixing frame, and an eyebrow-shaped light shield. The at least one light emitting element is located on the main body for projecting an illuminating light beam. The light shield fixing frame is located on the main body and surrounding the at least one light emitting element. The eyebrow-shaped light shield is detachably located on the light shield fixing frame and has an eyebrow-shaped transparent portion.

Wherein, when the at least one light emitting element projects the illuminating light beam toward the eyebrow-shaped light shield, the illuminating light beam would be shielded by the eyebrow-shaped light shield to form the eyebrow-shaped light beam projected from the eyebrow-shaped transparent portion to the eyebrow growing area.

In accordance with an embodiment of the present invention, the at least one light emitting assembly comprises a plurality of light emitting elements, and the light emitting elements are located on the main body and arranged as an eyebrow shape for projecting the at least one eyebrow-shaped light beam.

In accordance with an embodiment of the present invention, the at least one light emitting assembly comprises a plurality of light emitting elements, the light emitting elements are located on the main body and arranged as a matrix, and the light emitting elements are controlled by a program for projecting the at least one eyebrow-shaped light beam.

In accordance with an embodiment of the present invention, the wearable light emitting apparatus for eyebrow growth further comprises at least one light shield cover, located on the main body and surrounding the at least one light emitting assembly, and the at least one light shield cover being utilized for attaching and covering the eyebrow growing area when the main body is wore on the head of the user.

In accordance with an embodiment of the present invention, the main body further comprises a light emitting assembly placing portion and two extending arms. The at least one light emitting assembly is located on the light emitting assembly placing portion. The two extending arms are located at two sides of the light emitting assembly placing portion respectively for hugging two ears of the head. As a preferred embodiment, the wearable light emitting apparatus for eyebrow growth further comprises an elastic belt, which is detachably connected to the two extending arms for elastically mounting on the head.

As mentioned, the wearable light emitting apparatus for eyebrow growth provided in the present invention is capable to project light beams to the eyebrow growing area to promote hair growth in the eyebrow growing area. In addition, by using the eyebrow-shaped light beam, the eyebrow can be gradually modified to fit the shape of the eyebrow-shaped light beam.

The present invention will now be specified with reference to its preferred embodiment illustrated in the following drawings.

DESCRIPTION OF THE PREFERRED EMBODIMENT

The specific structural and functional details disclosed herein are only representative and are intended for describing exemplary embodiments of the disclosure. It is noted that, in the disclosure, similar elements would be represented by the same labels. Moreover, the drawings are for the purpose of illustration. The drawings may not be drawn based on precise proportions, and the drawing may not contain all the details.

Figure 1:
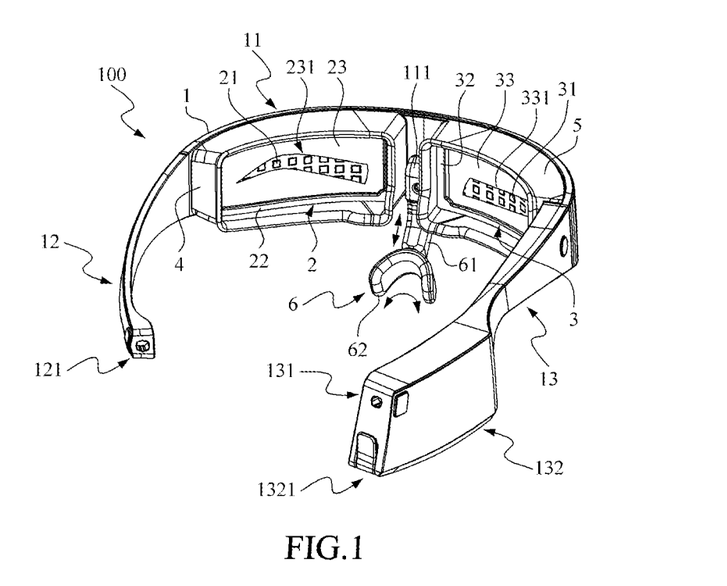
FIG. 1 is a 3D schematic view of a wearable light emitting apparatus for eyebrow growth provided in accordance with a first preferred embodiment of the present invention.
Figure 2:
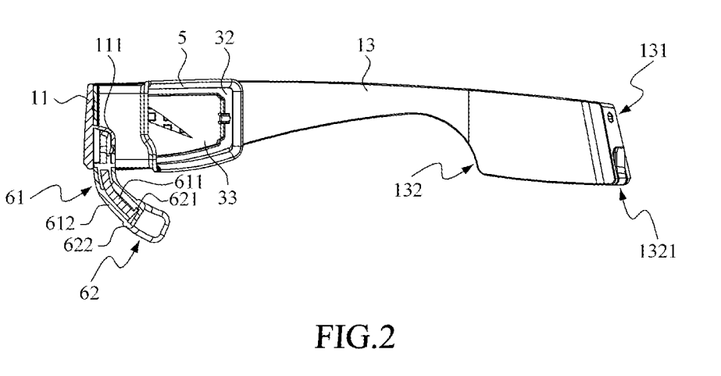
FIG. 2 is a cross-section view along A-A cross-section of FIG. 1.
Figure 3:
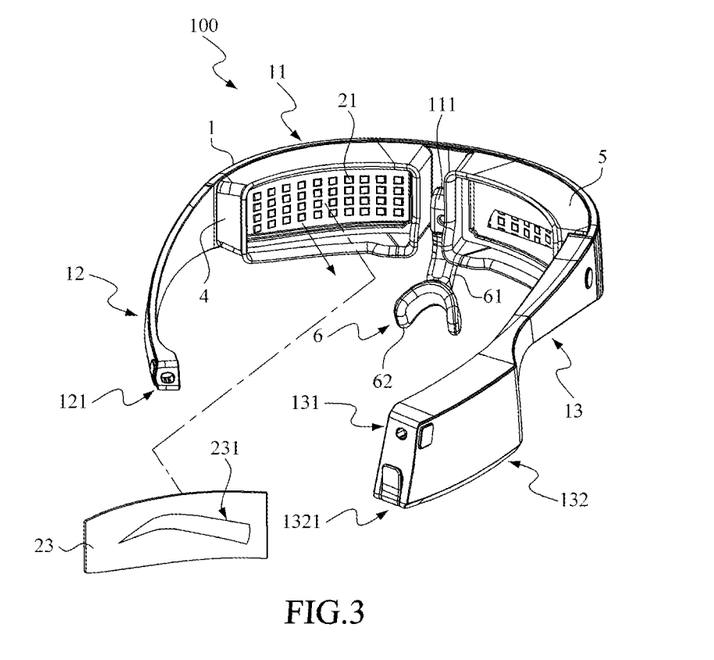
FIG. 3 is a 3D partial explosive view of the wearable light emitting apparatus for eyebrow growth provided in accordance with the first preferred embodiment of the present invention.

Please refer to FIG. 1 to FIG. 3, wherein FIG. 1 is a 3D schematic view of a wearable light emitting apparatus for eyebrow growth provided in accordance with a first preferred embodiment of the present invention, FIG. 2 is a cross-section view along A-A cross-section of FIG. 1, and FIG. 3 is a 3D partial explosive view of the wearable light emitting apparatus for eyebrow growth provided in accordance with the first preferred embodiment of the present invention. As shown, the wearable light emitting apparatus 100 for eyebrow growth includes a main body 1, a light emitting assembly 2, a light emitting assembly 3, a light shield cover 4, a light shield cover 5, and a supporting structure 6.

The main body 1 includes a light emitting assembly placing portion 11 and two extending arms 12 and 13. The light emitting assembly placing portion 11 has a fixing structure 111, and the two extending arms 12 and 13 are located at two sides of the light emitting assembly placing portion 11. In detail, the two extending arms 12 and 13 are extended from the two sides of the light emitting assembly placing portion 11 to compose an one-piece structure. The extending arm 12 has a belt fixture 121. In addition to a belt fixture 131, the extending arm 13 further has a battery seat 132 and a charging port 1321. A chargeable battery is placed in the battery seat 132, and the charging port 1321 is used to connect an external power source for charging the chargeable battery at the battery seat 132.

The light emitting assemblies 2 and 3 are located on the main body 1 and at the two sides of the fixing structure 111. The light emitting assemblies 2 and 3 are two similar structures symmetric with respect to the fixing structure 111. Take the light emitting assembly 2 as an example, the light emitting assembly 2 includes a plurality of light emitting elements 21 (only one of them is labelled), a light shield fixing frame 22, and an eyebrow-shaped light shield 23.

The light emitting elements 21 are located on the main body 1 for projecting a light beam (not labelled in the figure). The light shield fixing frame 22 is located on the main body 1 and surrounds the plurality of light emitting elements 21. The eyebrow-shaped light shield 23 is detachably located on the light shield fixing frame 22 and has an eyebrow-shaped transparent portion 231. The light emitting element 21 can be a light emitting diode (LED) in practice, and the plural light emitting elements 21 disclosed in the present embodiment can be regarded as a plurality of small LEDs. However, the present invention should not be limited thereto. For example, the light emitting assembly can be an one-piece LED panel disposed in the light shield fixing frame 22.

Moreover, the eyebrow-shaped light shield 23 in practice can be a plate structure formed by using acrylic or other epoxy materials, and the eyebrow-shaped transparent portion 231 can be a through hole or a transparent structure. As the eyebrow-shaped transparent portion 231 is a through hole, the eyebrow-shaped light shield 23 itself is formed by using an opaque material. As the eyebrow-shaped transparent portion 231 is a transparent structure, the eyebrow-shaped light shield 23 itself is formed of a transparent material but with printing, coating, or adhering an opaque layer on the region outside the eyebrow-shaped transparent portion 231 such that only the portion of the light beam aligning to the eyebrow-shaped transparent portion 231 would penetrating the eyebrow-shaped light shield 23 to form an eyebrow-shaped light beam. The eyebrow-shaped light beam indicates a light beam with an eyebrow-shaped light field, i.e. the projecting area of the light beam has a shape of an eyebrow.

The light emitting assemblies 3 include a plurality of light emitting elements 31 (only one of them is labelled in the figure), a light shield fixing frame 32, and an eyebrow-shaped light shield 33. Because the light emitting assembly 3 and 2 are similar and symmetric to each other, the detail about the light emitting assembly 3 is skipped.

Figure 4:
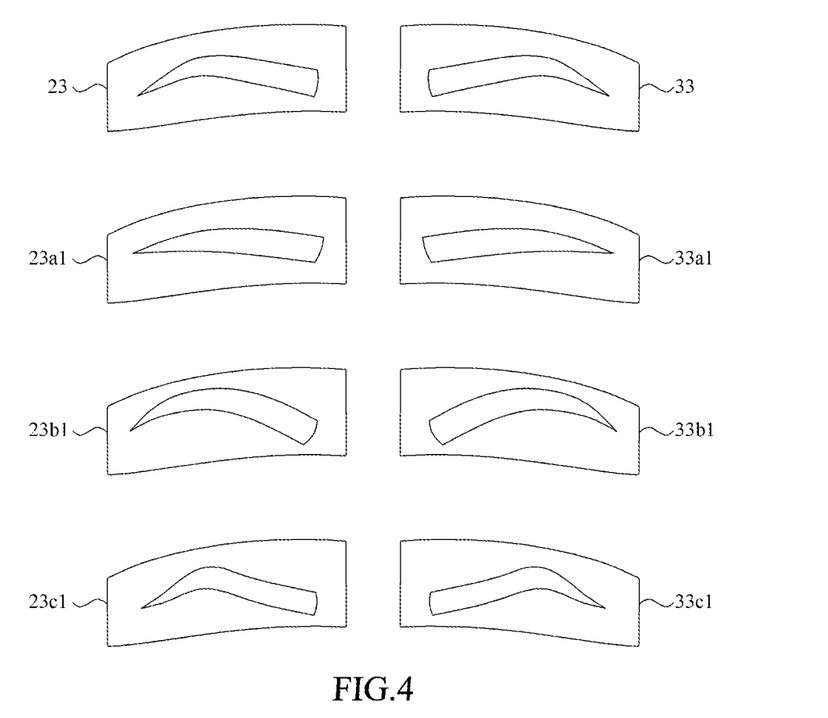
FIG. 4 is a planar schematic view of the eyebrow-shaped light shield provided in accordance with a first preferred embodiment of the present invention.

Please keep referring to FIG. 4, which is a planar schematic view of the eyebrow-shaped light shield provided in accordance with a first preferred embodiment of the present invention. As shown, in addition to the aforementioned eyebrow-shaped light shield 23 and the eyebrow-shaped light shield 33, the user may detach the eyebrow-shaped light shield 23 and the eyebrow-shaped light shield 33 from the light shield fixing frame 22 and the light shield fixing frame 32 respectively, and choose the other eyebrow-shaped light shield 23a1, 33a1, 23b1, 33b1, 23c1, or 33c1 according to the need in practice.

The light shield cover 4 and the light shield cover 5 are symmetrically located at the two sides of the main body 1 centered at the fixing structure 111. The light shield cover 4 and the light shield cover 5 are located around the light shield fixing frame 22 and the light shield fixing frame 32 to surround the light emitting assembly 2 and the light emitting assembly 3 respectively so as to prevent leakage of the light emitted by the light emitting assembly 2 and the light emitting assembly 3. In practice, the light shield cover 4 and the light shield cover 5 can be made of an opaque soft material, such as the silicone.

The supporting structure 6 is located on the main body 1. The supporting structure 6 includes an extending portion 61 and a pad portion 62. The extending portion 61 is detachably located on the fixing structure 111. The extending portion 61 includes an extending portion body 611 and an extending portion coating layer 612. The extending portion body 611 can be made of a metal or a plastic material, either soft or hard. The extending portion coating layer 612 covers the extending portion body 611 and is made of a soft plastic material such as silicone in practice. The pad portion 62 is connected to the extending portion 61, and includes a pad portion body 621 and a pad portion coating layer 622. The pad portion body 621 can be made of the material similar to that of the extending portion body 611, i.e. the pad portion body can be made of a metal or a plastic material, either soft or hard. In addition, in the present embodiment, the pad portion body 621 and the extending portion body 611 are integrated as an one-piece structure. The pad portion coating layer 622 can be made of the material similar to that of the extending portion coating layer 612, i.e. the pad portion coating layer 622 can be made of a soft plastic material, such as the silicone. In addition, in the present embodiment, the pad portion coating layer 622 may be integrated with to the extending portion coating layer 612.

Figure 5:
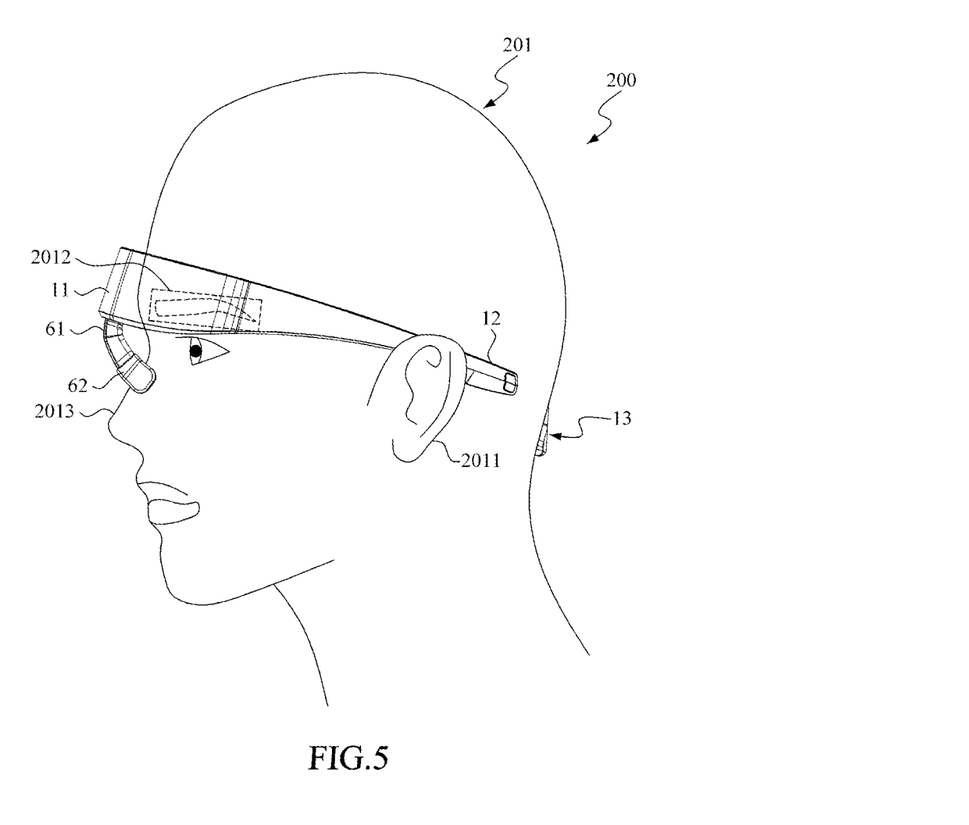
FIG. 5 is a schematic view showing an user wearing the wearable light emitting apparatus for eyebrow growth provided in accordance with the first preferred embodiment of the present invention and having the light emitting assembly aligning to the eyebrow growing area.

Please keep referring to FIG. 5, which is a schematic view showing an user wearing the wearable light emitting apparatus for eyebrow growth provided in accordance with the first preferred embodiment of the present invention and having the light emitting assembly aligning to the eyebrow growing area.

As shown, in practical application, the user 200 may put the extending arms 12 and 13 above the two ears 2011 (only the left ear is shown) of the head 201 respectively for hugging the ears 2011, and use the extending portion 61 lying on the nose bridge 2013 to press against the nose bridge 2013 to have the light shield covers 4 and 5 attaching and covering the eyebrow growing area 2012, so as to have the eyebrow-shaped light beam, which is formed by shielding the light beam emitted from the light emitting elements 21 and 31 by using the eyebrow-shaped light shields 23 and 33, projected to the eyebrow growing area 2012. Thereby, the hairs in the eyebrow growing area 2012 illuminated by the eyebrow-shaped light beam would be stimulated to promote hair growth, such that the eyebrow hairs can be modified gradually to fit the shape of the eyebrow-shaped transparent regions 231 and 331. In addition, the supporting structure 6 may prevent the wearable light emitting apparatus 100 from sliding down the nose effectively so as to prevent the eyebrow-shaped light beam from projecting to the eyes of the user 200.

Figure 6:
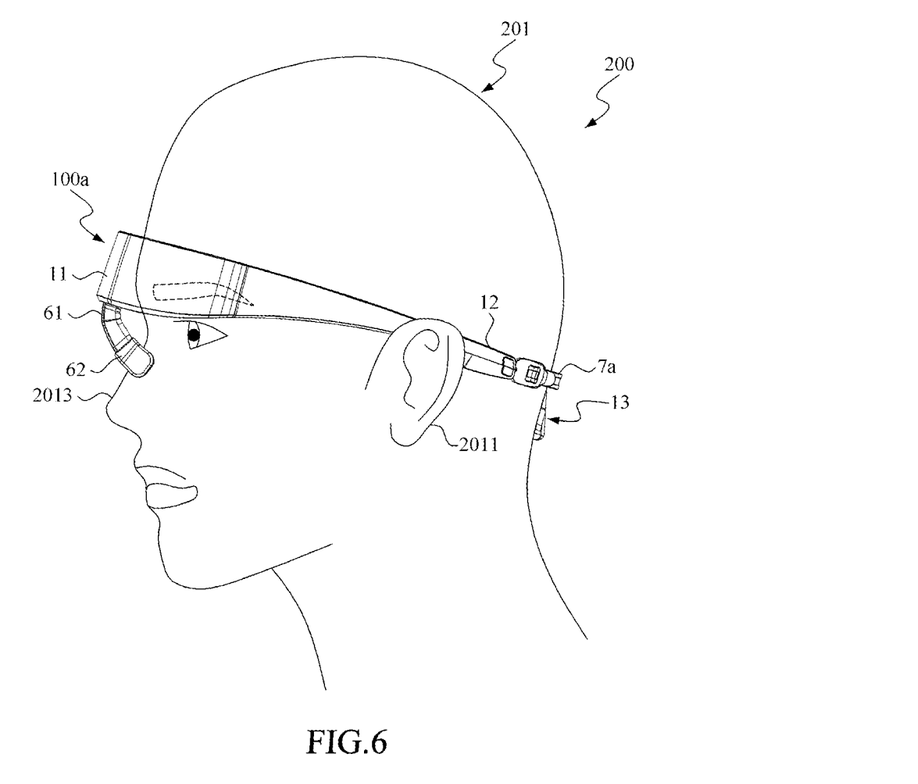
FIG. 6 is a schematic view showing an user wearing the wearable light emitting apparatus for eyebrow growth provided in accordance with a second preferred embodiment of the present invention on the head of the user.

Please keep referring to FIG. 6, which is a schematic view showing an user wearing the wearable light emitting apparatus for eyebrow growth provided in accordance with a second preferred embodiment of the present invention on the head of the user. As shown, the wearable light emitting apparatus 100a for eyebrow growth provided in the present invention is similar to the aforementioned wearable light emitting apparatus 100 for eyebrow growth. The only difference between the two apparatuses is that, the wearable light emitting apparatus 100a for eyebrow growth further comprises an elastic belt 7a. The elastic belt 7a is detachably connected to the two extending arms 12 and 13. When the user 200 puts the wearable light emitting apparatus 100a on the head 201, the elastic belt 7a is utilized for elastically mounting on the head 201 to enhance the stability of the wearable light emitting apparatus 100a on the head 201 effectively.

Figure 7:
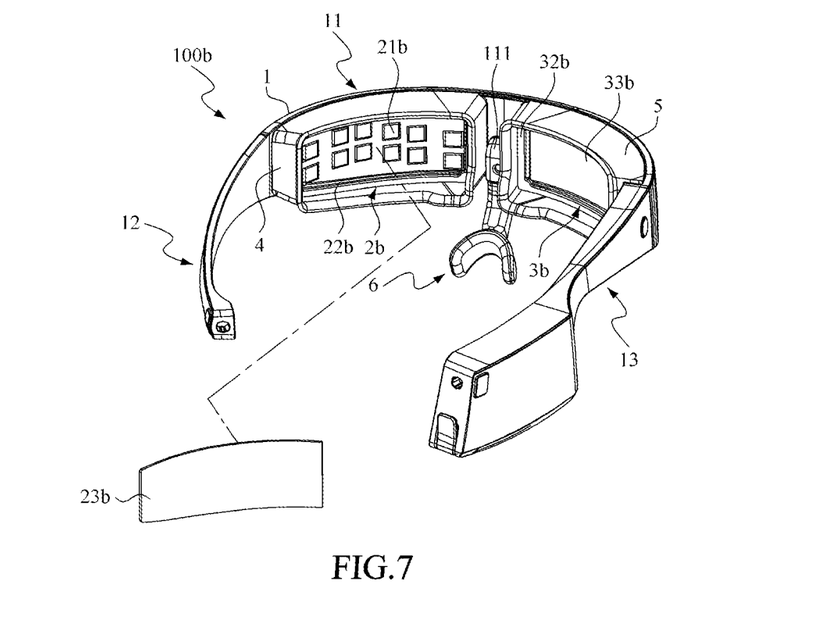
FIG. 7 is a 3D partial explosive view of the wearable light emitting apparatus for eyebrow growth provided in accordance with a third preferred embodiment of the present invention.

Please keep referring to FIG. 7, which is a 3D partial explosive view of the wearable light emitting apparatus for eyebrow growth provided in accordance with a third preferred embodiment of the present invention. As shown, the wearable light emitting apparatus 100b for eyebrow growth provided in the present invention includes a main body 1, a light emitting assembly 2b, a light emitting assembly 3b, a light shield cover 4, a light shield cover 5, and a supporting structure 6. The wearable light emitting apparatus 100b for eyebrow growth is similar to the wearable light emitting apparatus 100 for eyebrow growth, and the major difference between the two apparatuses is that the two light emitting assemblies 2b and 3b are used to replace the light emitting assemblies 2 and 3.

The light emitting assembly 2b includes a plurality of light emitting elements 21b (only one of them is labelled), a protective plate fixing frame 22b, and a transparent protective plate 23b. The plurality of light emitting elements 21b are arranged as an eyebrow shape for projecting the eyebrow-shaped light beam. The protective plate fixing frame 22b surrounds the plurality of light emitting elements 21b, and the transparent protective plate 23b is detachably fixed in the protective plate fixing frame 22b to protect the plurality of light emitting elements 21b from being hit.

The light emitting assembly 3b includes a plurality of light emitting elements (not shown), a protective plate fixing frame 32b and a transparent protective plate 33b. Because the light emitting assembly 3b and 2b are similar and symmetric to each other, the detail about the light emitting assembly 3b is skipped.

Figure 8:
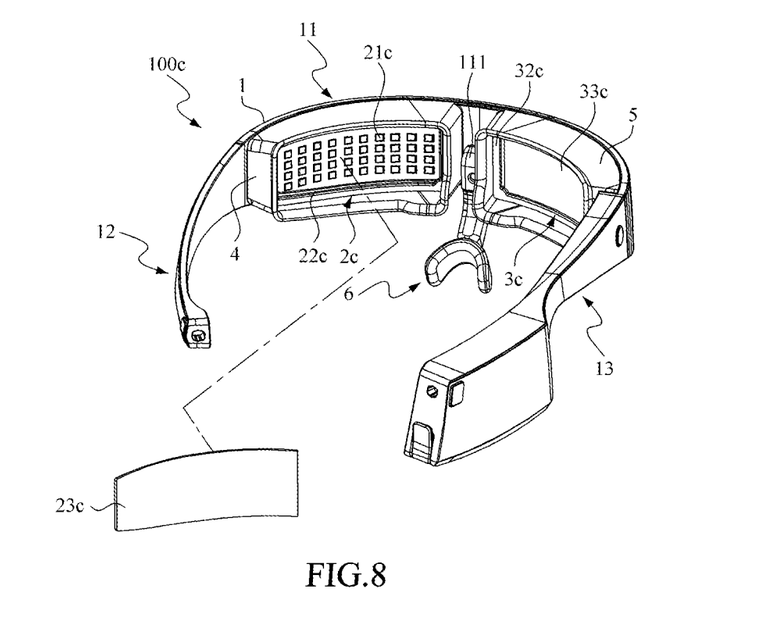
FIG. 8 is a 3D partial explosive view of the wearable light emitting apparatus for eyebrow growth provided in accordance with a fourth preferred embodiment of the present invention.
Figure 9:
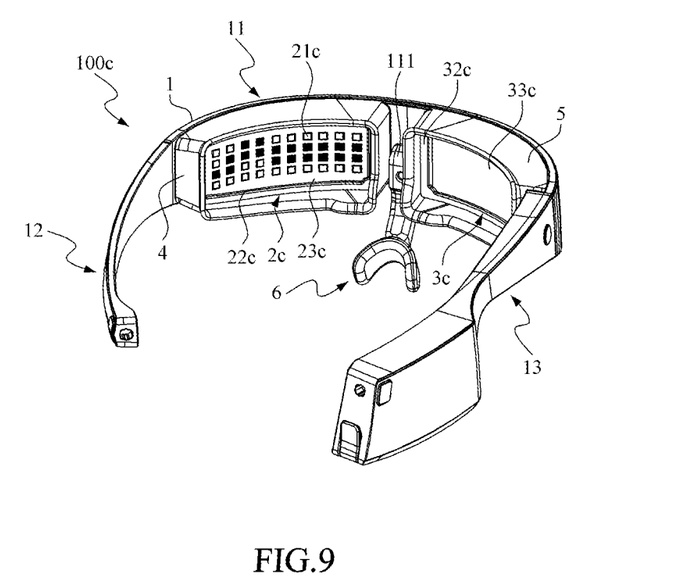
FIG. 9 is a 3D schematic view of the wearable light emitting apparatus for eyebrow growth provided in accordance with the fourth preferred embodiment of the present invention with a plurality light emitting elements illuminates according to a preset eyebrow shape.

Please keep referring to FIG. 8 and FIG. 9, wherein FIG. 8 is a 3D partial explosive view of the wearable light emitting apparatus for eyebrow growth provided in accordance with a fourth preferred embodiment of the present invention, and FIG. 9 is a 3D schematic view of the wearable light emitting apparatus for eyebrow growth provided in accordance with the fourth preferred embodiment of the present invention with a plurality light emitting elements illuminates according to a preset eyebrow shape. As shown, the wearable light emitting apparatus 100c for eyebrow growth provided in the present invention includes a main body 1, a light emitting assembly 2c, a light emitting assembly 3c, a light shield cover 4, a light shield cover 5, and a supporting structure 6. The wearable light emitting apparatus 100c for eyebrow growth is similar to the wearable light emitting apparatus 100 for eyebrow growth, and the major difference between the two apparatuses is that the two light emitting assemblies 2c and 3c are used to replace the light emitting assemblies 2 and 3.

The light emitting assembly 2c includes a plurality of light emitting elements 21c (only one of them is labelled), a protective plate fixing frame 22c, and a transparent protective plate 23c. The plurality of light emitting elements 21c are arranged as a matrix, and the light emitting elements 21c are controlled by a program for projecting the eyebrow-shaped light beam. In FIG. 8, all the light emitting elements 21c are in the unilluminated state, but as the user starts up the light emitting assembly 2c, as shown in FIG. 9, the light emitting assembly 2c would switch some of the light emitting elements to the illuminated state (i.e. the solid ones) according to the predetermined eyebrow shape so as to project the eyebrow-shaped light beam. In practical application, the wearable light emitting apparatus 100c may use an embedded controller to control the individual illumination state of each of the plurality of light emitting elements 21c through a program, or have the individual illumination state of each of the plurality of light emitting elements 21c controlled by the program from another electronic device through wireless communication.

The protective plate fixing frame 22c surrounds the plurality of light emitting elements 21c, and the transparent protective plate 23c is detachably fixed in the protective plate fixing frame 22c to protect the plurality of light emitting elements 21c from being hit.

The light emitting assembly 3c includes a plurality of light emitting elements (not shown), a protective plate fixing frame 32c and a transparent protective plate 33c. Because the light emitting assembly 3c and 2c are similar and symmetric to each other, the detail about the light emitting assembly 3c is skipped In conclusion, the wearable light emitting apparatus for eyebrow growth provided in the present invention is capable to project an eyebrow-shaped light beam to the eyebrow growing area to stimulate hair growth for the hairs under illumination, and the wearable light emitting apparatus for eyebrow growth is also capable to gradually modify the eyebrows shape to fit the shape of the eyebrow-shaped light beam. Thus, in compared with the conventional shaping technologies, which may influence the growth of eyebrow hairs because the shaping process is executed manually, the wearable light emitting apparatus for eyebrow growth provided in the present invention has the feature to stimulate hair growth by illumination and use the eyebrow-shape light beam to gradually modify the shape of eyebrow to fit the shape of the eyebrow-shape light beam such that it is not necessary to touch the eyebrow growing area. In addition, because the eyebrow hairs grow by themselves under the stimulation of light beams, the shape of the eyebrow would be more natural.

The shape of the eyebrow-shaped light beam can be modified by using the eyebrow-shaped light shield, by arranging the light emitting elements according to the wanted eyebrow shape, or by using a program to turn on a portion of the plurality of light emitting elements arranged as a matrix according to the eyebrow shape.

In addition, because the wearable light emitting apparatus for eyebrow growth further has a supporting structure and an elastic belt, the main body can be supported by the supporting structure lying on the nose bridge or mounted on the head of the user by the elastic belt, so as to have the eyebrow-shaped light beam aligning to the eyebrow growing area more stable.

While the present invention has been particularly shown and described with reference to a preferred embodiment, it will be understood by those skilled in the art that various changes in form and detail may be without departing from the spirit and scope of the present invention.

What is claimed is:

1. A wearable light emitting apparatus for eyebrow growth, comprising:
   a main body, to be wore on an user's head;
   at least one light emitting assembly for projecting at least one eyebrow-shaped light beam to an eyebrow growing area of the head when the main body is wore on the user's head,
   wherein each of the at least one light emitting assembly comprises:
   a plurality of light emitting elements, located on the main body and arranged as an eyebrow shape for projecting illuminating light beams;
   a light shield fixing frame, located on the main body and surrounding the plurality of light emitting elements; and
   an eyebrow-shaped light shield, detachably located on the light shield fixing frame and having an eyebrow-shaped transparent portion;
   wherein, when the plurality of light emitting elements projects the illuminating light beams toward the eyebrow-shaped light shield, the illuminating light beams are shielded by the eyebrow-shaped light shield to form the at least one eyebrow-shaped light beam projected from the eyebrow-shaped transparent portion to the eyebrow growing area.

2. The wearable light emitting apparatus for eyebrow growth of claim 1, further comprising at least one light shield cover, located on the main body and surrounding the at least one light emitting assembly, and the at least one light shield cover being utilized for attaching and covering the eyebrow growing area when the main body is wore on the head of the user.

3. The wearable light emitting apparatus for eyebrow growth of claim 1, further comprising a supporting structure, located on the main body for lying on a nose bridge of the head.

4. The wearable light emitting apparatus for eyebrow growth of claim 1, wherein the main body further comprises:
   a light emitting assembly placing portion, and the at least one light emitting assembly being located on the light emitting assembly placing portion; and
   two extending arms, located at two sides of the light emitting assembly placing portion respectively, for hugging two ears of the head.

5. The wearable light emitting apparatus for eyebrow growth of claim 4, further comprising an elastic belt, detachably connected to the two extending arms for elastically mounting on the head.

* * * * *